United States Patent [19]
Ayers et al.

[11] Patent Number: 5,885,843
[45] Date of Patent: Mar. 23, 1999

[54] DEVICE AND METHOD FOR DETERMINING OXYGEN CONCENTRATION AND PRESSURE IN GASES

[75] Inventors: Michael R. Ayers, El Cerrito; Arlon J. Hunt, Kensington, both of Calif.

[73] Assignee: The Regents of the University of California, Oakland, Calif.

[21] Appl. No.: 815,290

[22] Filed: Mar. 7, 1997

Related U.S. Application Data

[63] Continuation-in-part of Ser. No. 698,980, Aug. 16, 1996.

[51] Int. Cl.$^6$ ................................................... G01N 21/64
[52] U.S. Cl. .......................... 436/136; 436/68; 436/172; 422/82.05; 422/82.08; 422/91
[58] Field of Search .............................. 422/82.06, 82.07, 422/82.08, 82.05, 91; 436/68, 136, 137, 138, 164, 166, 172

[56] References Cited

U.S. PATENT DOCUMENTS

| | | | |
|---|---|---|---|
| 5,063,164 | 11/1991 | Goldstein | 436/169 |
| 5,352,582 | 10/1994 | Lichtenwalter et al. | 435/6 |
| 5,501,836 | 3/1996 | Myerson | 422/57 |
| 5,618,493 | 4/1997 | Goldstein et al. | 422/57 |

OTHER PUBLICATIONS

Bacon, J. R. et al., *Photophysics and Photochemistry of Oxygen Sensors Based on Luminescent Transition–Metal Complexes*, 1991, American Chemical Society, 63, 337–342.

Baron, A. E. et al., *Submillisecond Response Times of Oxygen–quenched Luminescent Coatings*, Dec. 1993, Rev. Sci. Instrum., 64 (12), 3394–3402.

Degraff, B. A. et al., *Design of Oxygen Sensors Based on Quenching of Luminescent Metal Complexes: Effect of Ligand Size on Heterogeneity*, 1993, Anal. Chem. 65, 3480–3483.

Degraff, B. A. et al., *Oxygen Sensors Based on Luminescence Quenching: Interactions of Metal Complexes with the Polymer Supports*, 1994, Anal. Chem., 66, 4133–4141.

Delpy, D. T. and Gewehr, P.M., *Optical Oxygen Sensor Based on Phosphorescence Lifetime Quenching and Employing a Polymer Immobilised Metalloporphyrin Probe*, Jan. 1993, Medical & Biological Engineering & Computing, 31, 2–10.

Fricke, J., et al., *Aerogels—Nanoporous Materials Part I: Sol–Gel Process and Drying of Gels*, J. Porous Materials, 1, 1 (1995).

Hartmann, P., et al. *Luminescence Quenching Behavior of an Oxygen Sensor Based on a Ru(II) Complex Dissolved in Polystyrene*, Jan. 1, 1995, Anal Chem., 67, 88–93.

Henkel, S. vL., *Research and Developments—Silica Aerogels Are Put to Work Detecting Gaseous $O_2$*, Jun. 1996, Sensors, 10 & 12.

Hunt, A. J. et al., *Ambient–Temperature Supercritical Drying of Transparent Silica Aerogels*, Mater. Lett., 1995, 3, 363.

Lee, W., et al, *Luminescent Dicyanoplatinum (II) Complexes as Sensors for the Optical Measurement of Oxygen Concentrations*, 1993, Anal. Chem., 65, 255–258.

Parmenter, C. S., et al., *Fluorescence Quenching in Aromatic Hydrocarbons by Oxygen*, 1969, J. Chem. Phys., 51, 2242.

Yokogawa, H. et al., *Hydrophobic Silica Aerogels*, J. Non-–Cryst. Solids, 186, 23–29.

*Optical Oxygen Sensor Based on Silica Aerogel*,(downloaded Jan. 8, 1997), http://eande.lbl.gov/ECS/aerogels/sao2sens.htm.

*Primary Examiner*—Jeffrey Snay
*Attorney, Agent, or Firm*—Paul R. Martin; Hickman Beyer & Weaver, LLP

[57] ABSTRACT

Disclosed are oxygen concentration and/or pressure sensing devices and methods which incorporate photoluminescent silica aerogels. Disclosed sensors include a light proof housing for holding the photoluminescent aerogel, a source of excitation radiation (e.g., a UV source), a detector for detecting radiation emitted by the aerogel, a system for delivering a sample gas to the aerogel, and a thermocouple. Also disclosed are water resistant oxygen sensors having a photoluminescent aerogel coated with a hydrophobic material.

32 Claims, 6 Drawing Sheets

DEVICE AND METHOD FOR DETERMINING OXYGEN CONCENTRATION AND PRESSURE IN GASES

CROSS REFERENCE TO RELATED APPLICATIONS

This application is a continuation-in-part of U.S. patent application Ser. No. 08/698,980 entitled "Process for the Chemical Modification of Inorganic Aerogels", filed Aug. 16, 1996, the disclosure of which is incorporated by reference in its entirety herein.

This invention was made in the course of or under prime contract number DE-AC03-76SF00098 between the U.S. Department of Energy and the University of California. The government has certain rights in this invention.

FIELD OF THE INVENTION

The present invention relates to devices and methods for determining oxygen concentration and/or pressure in a gas. More specifically, the invention relates to oxygen concentration and pressure detection devices and methods which incorporate photoluminescent silica aerogels.

BACKGROUND OF THE INVENTION

Oxygen sensors are used in a variety of applications in a variety of fields, including medicine, industry and scientific research. Commercially used oxygen sensors employ several different detection mechanisms, including electrochemical cells, and high temperature ionic conductors, such as solid state oxygen ion conduction based sensors, for instance, zirconia-based oxygen sensors in automobiles. However, these systems generally have relatively slow response times (because, for instance, gases must be transported through an electrolyte for detection to occur), or, as with the zirconia-based systems, require high operating temperatures.

Other oxygen sensors are optically based. Several devices have been proposed based on the luminescence quenching of various organic or inorganic materials which are typically dispersed in a polymer matrix. These materials permit the detection of oxygen concentration through a phenomenon known as photoluminescence "quenching".

In general terms, photoluminescence occurs when a material absorbs a photon of sufficient energy. The entity that absorbs the photon may be a discrete molecule, or a defect center in a solid-state material, for example, and is often referred to as a "carrier." When the photon has been absorbed, the carrier is moved into a high-energy, excited state. After a certain length of time, the carrier will relax back to its ground state. In so doing, it emits light. The lifetime of the excited state is usually on the order of nanoseconds to microseconds. The mechanism by which the carrier relaxes determines whether the photoluminescence is generally termed "fluorescence" or "phosphorescence." If the luminescence persists significantly after the excitation cause is removed, it is called phosphorescence; if it does not, it is called fluorescence.

If an oxygen molecule collides with a carrier while it is in its excited state, the oxygen molecule can absorb the carrier's excess energy and "quench" the photoluminescence. Quenching occurs when the oxygen molecule absorbs the energy and undergoes a triplet-to-singlet transition, while the carrier undergoes a nonradiative relaxation. The efficiency of the photoluminescence quenching is therefore determined by the number of collisions between the material containing the carrier, and oxygen molecules. Because the collision frequency of gases is determined by the concentration of quenching molecules present, the pressure and the temperature, the quenching efficiency for a given pressure and temperature, and consequently the photoluminescence intensity, will be determined by the concentration of oxygen in the atmosphere surrounding the material.

Various oxygen sensors based on the quenching of photoluminescent materials are known in the art. Examples of phosphorescent/photoluminescent materials used in oxygen sensors include a polymer immobilized metalloporphyrin (see Gewehr, P. M., Optical Oxygen Sensor Based on Phosphorescent Lifetime Quenching and Employing a Polymer Immobilized Metalloporphyrin Probe, *Med. & Bio. Eng. & Compute* 31, 2–10 (1993), transition-metal complexes (E. R. Carraway, et al., Photophysics and Photochemistry of Oxygen Sensors Based on Illuminescent Transition Metal Complexes, *Anal. Chem.* 63, 337–342 (1991), and dicyanoplatinum (II) complexes (Illuminescent dicyanoplatinum (II) complexes as sensors for the optical measurement of oxygen concentrations, W. W. Lee, et al., *Anal. Chem.* 5, 255–258 (1993), among others. See also, P. Hartmann, et al., Luminescence Quenching Behavior of an Oxygen Sensor Based on a Ru(II) Complex Dissolved in Polystyrene, *Anal. Chem.* 67, 88–93 (1995); W. Xu, et al., Oxygen Sensors Based on Luminescence Quenching: Interactions of Metal Complexes with the Polymer Substrates, *Anal. Chem.* 66, 4133–4141 (1994); A. E. Baron, et al., Submillisecond response times of oxygen-quenched luminescent coatings, *Rev. Sci. Instrum.* 64, 3394–3402 (1993); L. Sacksteder, Design of Oxygen Sensors Based on Quenching of Luminescent Metal Complexes: Effect of Ligand Size on Heterogeneity, *Anal. Chem.* 65, 3480–3483 (1993).

All of these materials have drawbacks. Many, particularly the organic materials, are susceptible to bleaching in a relatively short period of time. Bleaching adversely affects their photoluminescent character and thus shortens their useful lifetime. In addition, many of these materials are unstable at high temperatures and many have a slow response time, since in many cases oxygen must diffuse or otherwise migrate through a polymer (e.g., silicone) matrix in order to reach the photoluminescent material.

Accordingly, there is a need for improved oxygen sensors.

SUMMARY OF THE INVENTION

The present invention provides improved oxygen sensors based on the oxygen quenching of photoluminescent silica aerogels. These aerogel based sensors provide a rapid response time due to rapid diffusion of sample gases within the aerogel pore network. The photoluminescent aerogel materials also resist photo bleaching and are stable across a wide range of temperatures. Thus, aerogel-based oxygen sensors have a longer lifetime and are more reliable in extreme environments as compared to many prior art sensors.

An oxygen sensing device according to a preferred embodiment of the present invention may include a light proof housing in which a photoluminescent silica aerogel is placed. The device includes a source of radiation for providing excitation energy to the aerogel and a detector for detecting light emitted from the aerogel. The device is also equipped with an interface for bringing a gas phase sample into contact with the aerogel. Any oxygen contained in the sample reduces photoluminescent emissions from the aerogel by an amount related to the oxygen concentration or pressure in the sample. The device may be equipped to signal a change in oxygen concentration and/or pressure in a sample or to quantify oxygen concentration and/or pressure in a sample.

The invention also provides a method for determining a change in concentration and/or pressure of oxygen in a gas phase sample. In a preferred embodiment, the method involves irradiating a photoluminescent silica aerogel contained within a light proof housing with a source of excitation energy, bringing an oxygen-containing gas phase sample into contact with the photoluminescent silica aerogel, and detecting light emitted from the photoluminescent silica aerogel in the presence of the gas phase sample. The method may include a calibration step, and may quantify or signal a change in oxygen concentration and/or pressure.

The invention further provides a water-resistant photoluminescent silica aerogel for use in an oxygen detector, as well as methods for making such water-resistant photoluminescent silica aerogels.

The advantages of the present invention will become clear to those skilled in the art upon a study of the drawings and detailed description of the invention.

DETAILED DESCRIPTION OF THE INVENTION

Figure 1:
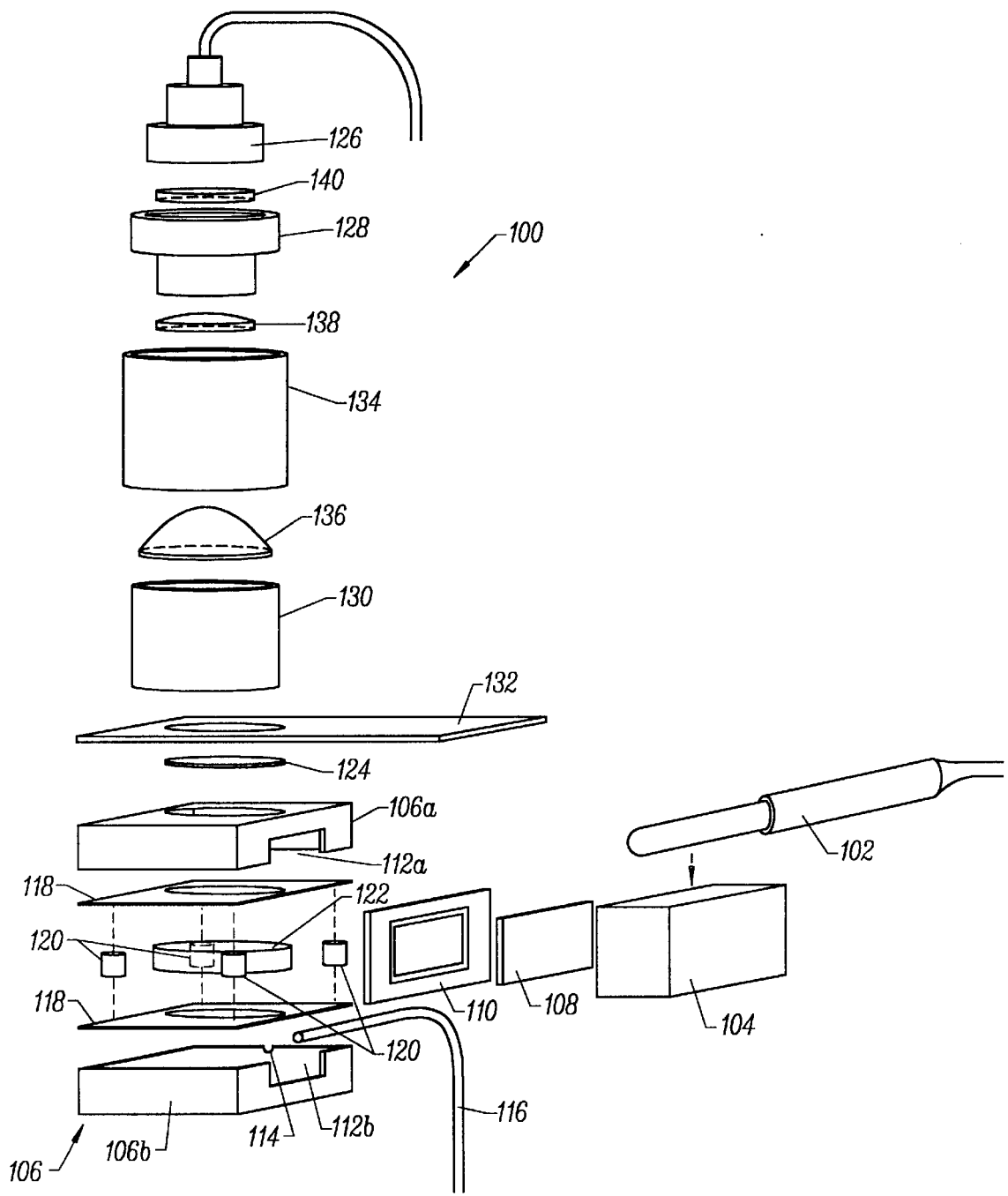
FIG. 1 shows an oxygen sensor in accordance with the present invention.

The present invention provides improved oxygen sensors based on the oxygen quenching properties of photoluminescent silica aerogels. An aerogel is the material resulting when the liquid part of a gel is removed without damaging the remaining solid part of the gel. Aerogels are most often prepared by supercritical extraction, controlled evaporation, or freeze drying. Generally, the aerogel will retain the original shape of the gel, be free of cracks, and occupy at least fifty percent of the original gel's volume. They may be made in silica, organic, and pure carbon forms, and generally have densities in the 0.08–1.15 gram per cubic centimeter (gm/cc) range. Silica and carbon aerogels are resistant to structural breakdown caused by solar radiation, radioactivity, and ozone. They are stable at temperatures greater than 500° C. and have thermal insulation characteristics three to ten times those of conventional organic foams or mineral wools—at a fraction of the weight.

The following terms may be useful in understanding aerogel structure, properties and applications. They should not be construed as limiting the scope of the invention.

"Sol" refers to a solution of polymeric or colloidal materials. A sol has many physical properties in common with normal solutions, however the suspended or polymeric or colloidal materials may be continuously agglomerating, leading to the formation of a gel.

"Gel" refers to a material composed of two phases, generally having a three-dimensional network of solid material and corresponding areas of free space. The solid part results from the agglomeration of sol particles. The liquid part of the gel fills the free space within the solid part. The liquid and solid parts of a gel generally occupy approximately the same volume of space.

"Pore" refers to open space in the structure of a material. The pore diameters of silica aerogels may range from approximately 2 to approximately 100 nanometers. For the purposes of this invention, the pores are preferably generally open and connected to one another allowing for volatile material to pass from one pore to the next, and eventually through the entire aerogel. As a result, at equilibrium, the composition of the atmosphere surrounding an aerogel is the same as that within the aerogel.

"Monolith" refers to a single piece of crack-free aerogel with a definite shape. Aerogel monoliths may be made into virtually any shape. Since the solid structure of aerogels consist of a three-dimensional polymeric network, aerogel monoliths can be thought of as single, extremely large, molecules (e.g., of $SiO_2$).

"Aerogel powder" refers to aerogel monoliths which are pulverized into powders. On a macroscopic scale, the resulting material is composed of small, free-flowing granules surrounded by free space. On a microscopic scale, the granules themselves retain the original pore structure of the aerogel. Therefore, aerogel powders possess a bi-modal pore structure of large pores between the granules and small pores within the granules.

"Xerogel" refers to a gel that has been dried without using methods that form aerogels. They are often cracked, have much higher densities than aerogels, and are less gas permeable than aerogels. Nevertheless, photoluminescent xerogels may be employed in the present invention.

The present invention uses photoluminescent aerogels having well-defined properties. In one embodiment, such aerogels may be formed from an inorganic aerogel (preferably silica) as an initial starting material. The initial aerogel is produced by any conventional procedure. For example, suitable aerogels may be made by sol-gel processing followed by supercritical extraction of entrapped solvents. In this case, a combination of reacting fluids and solvents are first mixed together to form a gel. To remove the solvent without destroying or altering the solid network, the gel is placed in a vessel and the temperature and pressure are raised above the critical point of the contained solvent. Thereafter, the pressure is released. The resulting material is an aerogel. Examples of preparation methods for initial aerogels useful in the present invention may be found in the U.S. Patents and articles cited in application Ser. No. 08/698, 980, which are incorporated herein by reference. Additional information on the preparation of aerogels may be found in J. Fricke, *J. Porous Materials*, 1, 1, (1995).

The initial aerogel will generally have characteristic morphological properties. It generally contains a particular network of open and interconnected pores. Prior to its modification, the aerogel's pore structure generally includes pores of specific diameters. The size of the pores is usually less than about 100 nanometers (nm) and preferably from between about 2 to about 100 nm. The specific pore structure within the aerogel considerably increases the internal surface of the aerogel relative to its external surface. For example, a piece of silica aerogel in the shape of a cube one (1) centimeter on edge may have an external surface area of approximately 6 $cm^2$ and an internal surface area of approximately 800,000 $cm^2$. The initial aerogel may be of any convenient size or shape. The initial aerogel may also exhibit any amount of visible transparency, but is preferably highly visibly transparent for the purposes of the present invention.

In addition to morphological properties, the initial aerogel may also be defined by characteristic functional properties.

These properties include distinctive chemical reactivity characteristics, mechanical properties, abilities to form composite materials, electrical properties, magnetic properties, optical properties, and varying resistance thermal, chemical, and radiation damage. Silica aerogels' transparency in the visible region of the electromagnetic spectrum, high surface area, facile transport of gases through the material, thermal and chemical stability, and ability to be filled with additional active phases are the key properties that make aerogels good candidates for sensor applications.

As noted, silica aerogels suitable for use with this invention may be modified to induce a permanent, visible photoluminescence. U.S. patent application Ser. No. 08/698,980 (previously incorporated by reference) describes processes by which silica aerogels may be modified in order to induce this photoluminescent character. It has been found that when a silica aerogel is exposed to a strongly reducing atmosphere, the resulting material can become photoluminescent. In one example, the initial aerogel is modified by first placing it within a reaction vessel and then exposing it to a specific gas or gas mixture under plasma forming conditions. One method of exposure is to fill the reaction vessel with the gas. Exposure times will depend on the type of aerogel and gases used.

The modifying gas will include at least one reducing gas. Examples of suitable reducing gases include $H_2$, $D_2$, $NH_3$, $ND_3$, $N_2$, NO, CO, $CH_4$, $C_2H_6$, $C_2H_2$, $C_3H_8$ (and other hydrocarbons), $CH_3F$, $B_2H_6$, $B_4H_{10}$, $H_2S$, $H_2Se$, $H_2Te$, $PH_3$, $AsH_3$, $SbH_3$, $SiH_4$, $Si_2H_6$, $SiH_3Cl$, $GeH_4$, $Ge_2H_6$, and $SnH_4$. Preferably the reducing gas is selected from $CH_4$, $H_2$, $NH_3$, or CO. The gas may further be diluted with noble (inert) gas such as He, Ne, Ar, Kr, and Xe, for instance, to reduce the reactivity of pyrophoric gases. Preferably the noble gas is selected from He, Ne, or Ar.

To form a plasma, the aerogel environment is next exposed to a radiation from any conventional electromagnetic radiation transmitter source. The type of radiation used is preferably in the microwave or radio frequency range. The frequency of the radiation is preferably a frequency that is not absorbed by the aerogel sample.

The length of time which the aerogel is exposed to a reducing plasma is between about 5 and about 960 minutes, preferably between about 5 and about 450 minutes and more preferably between about 5 and about 60 minutes. During exposure to the electromagnetic field, the temperature of the aerogel is maintained to preserve the structural composition of the aerogel. If the aerogel is subjected to high temperature (e.g., above 200° C.), the aerogel may shrink, crack, or melt. The optimal temperature depends on the type of aerogel, but generally the temperature remains low relative to the conditions needed to allow solid-gas reactions with aerogels. Typically, the aerogel temperature is maintained about 50° to 200° C., preferably between about 75° to about 175° C. and more preferably between about 100° and 150° C.

For example, a silica aerogel may be exposed to a reducing plasma while maintaining the temperature below about 200° C. in order to preserve its structural composition.

Treatment with microwave-energized reducing gases has been observed to produce strong visible photoluminescence in silica aerogel monoliths. Samples of up to one centimeter in thickness have shown photoluminescence throughout the entire volume of the monolith following treatment. Both the macroscopic and microscopic structure of the aerogel survived the reducing process unchanged. Chemical analysis of the material generally shows no apparent change in composition as a result of the plasma treatment, while NMR analysis may reveal a change in the Si—O connectivity. The most important distinction between a conventional aerogel and one suitable for use with this invention is an absorption spectrum in which light of a defined wavelength range is strongly absorbed and an emission spectrum in which light outside the absorption range is emitted. For example, a preferred aerogel absorbs UV radiation of wavelengths ranging from about 300–400 nanometers (nm), and emits visible light in a band centered at about 490 nm. The intensity of this emission varies inversely with the amount of gaseous oxygen within and surrounding the aerogel (at a given temperature). This inverse relationship varies with conditions, but generally follows the Stern-Volmer equation:

$$I_O/I = 1 + K_{sv}[Q]$$

where $I_O$=emission intensity without quencher ($O_2$); I=emission intensity with quencher ($O_2$); $K_{sv}$=Stern-Volmer constant (specific to material); and [Q]=concentration of quencher ($O_2$).

It is believed that the observed photoluminescence results from defects generated in the aerogel lattice structure by the reducing plasma. These defect centers absorb UV radiation and transition to an excited state, and then emit visible light on relaxation. For the purposes of this invention, a primary signature of the modified silica aerogels is their optical spectra. In general, modified silica aerogels having an irradiance of at least about 10 pW/cm$^2$ of bulk aerogel area may be used in the present invention. The modified silica aerogels show substantially more photoluminescence than unmodified silica aerogels. In a preferred embodiment, modified and unmodified aerogel emissions are readily distinguishable since the photoluminescence of the modified aerogels may be visible to the naked eye, whereas that of the unmodified aerogel is not.

Consistent with the defect theory, it has been found that the photoluminescent silica aerogels of the present invention generally perform better when the original aerogel is maintained in a highly strained or unrelaxed state, since the bond strain inherent in such a structure increases the number of defect centers introduced in the material following exposure to a reducing plasma. To preserve the native unrelaxed structure, the silica aerogel should not be baked or annealed as is conventionally done to reduce internal stress. Generally, however, any aerogel material that emits visible light in response to UV excitation is suitable for use in the devices and methods of the present invention.

The devices of the present invention will be described in terms of a preferred embodiment illustrated in FIG. 1. It will be clear to those of skill in the art that the present invention may have many other specific implementations, and is not limited to the embodiment described herein.

FIG. 1 shows an oxygen sensor 100 in accordance with the present invention. For clarity of description, the device 100 is shown in an exploded view of its constituent parts. When fully assembled, the parts form a light-tight housing. The device 100 includes a light source 102 (which will usually be a UV source), such as a mercury-arc lamp, a UV light emitting diode (LED), a semi-conductor laser, or any other source providing electromagnetic radiation of an appropriate wavelength and intensity. In this instance, source 102 is a mercury arc pen lamp (which will emit UV radiation centered at a wavelength of about 330 nm) located within a lamp housing 104 at one end of the device 100. The lamp housing 104 is separated from a sample enclosure 106 by a transverse window 108 composed of a material which permits the transmission of UV radiation. For example, this window may be composed of glass or fused silica and may be held in place by a frame 110, which separates the lamp housing 104 from the sample enclosure 106. Preferably, window 108 filters visible light while passing UV light. This prevents any visible radiation from the source from finding its way to the detector where it would be erroneously read as signal.

In the embodiment depicted in FIG. 1, the sample enclosure 106 is divided into a top portion 106*a* and a bottom portion 106*b* having slots 112*a* and 112*b* to accommodate window 108 and frame 110 in order to provide access for excitation light from lamp 102. The sample enclosure 106 also includes a hole 114 to accommodate a gas inlet conduit 116 to provide access for a gas to be sensed.

The sample enclosure 106 contains holders 118 and spacers 120 to support a photoluminescent aerogel material 122. The volume of the sample enclosure 106 is preferably kept to a minimum in order to provide the fastest possible response time. Obviously, larger enclosures have longer residence times. The enclosure 106 also has a second window 124 to permit the egress of visible light emitted by the photoluminescent aerogel from the sample enclosure 106. This window may be composed of any material which efficiently transmits visible light such as quartz or glass. Preferably, window 124 also filters UV radiation.

In the embodiment shown in FIG. 1, the window 124 is positioned at 90 degrees from the line of entry for the UV excitation radiation through window 108. That is, windows 124 and 108 are oriented at an angle of 90°. This is to prevent spurious visible source radiation from reaching the detector. Generally, windows 124 and 108 may be oriented at any angle relative to one another. However, angles at and approaching 180 degrees, measures must be employed to ensure that all visible radiation from source 102 is blocked.

The photoluminescent aerogel 122 may take many forms. As shown in FIG. 1, the aerogel is in the form of an unfixed monolith. However, the aerogel monolith may also be bound to a substrate, or it may be ground up to form an aerogel powder which is distributed in or on a support material, such as a mesh or a continuous substrate. Generally, any form of aerogel that exhibits the desired photoluminescence in response to exposure to an excitation energy may be used in the present invention.

A transparent aerogel can be positioned at any angle with respect to UV source 102 and detector 126 within sample enclosure 106. As shown in FIG. 1, the aerogel's principle surface is positioned at a 90 degree angle to the excitation source 102. However, maximum efficiency is achieved by orientating the aerogel in a direction that presents maximum surface area to both the excitation radiation and the emission radiation. This is generally achieved by orienting the largest surface of the aerogel 122 at an angle midway between the entry line of the UV light and the exit line of the visible light. In the embodiment shown in FIG. 1, a 45 degree orientation of the aerogel monolith 122 would achieve this purpose.

Visible light exiting the sample enclosure 106 through window 124 is permitted to contact a visible light detector 126. The detector/light measuring device may be a photodiode, a photo multiplier, or any other available device suitable for the purpose. The visible light detector area may be as large as the projected aerogel surface area in order to maximize system sensitivity. In one specific embodiment, a silicon photodiode which measures emissions optimally at 500 nanometers is used. The detector 126 is contained within a 128 which may be immediately adjacent to window 124. Alternatively, and as shown in FIG. 1, one or more filters or other optical elements may be interposed between window 124 and detector 126 in order to adequately shield the detector 126 from UV light emitted by source 102 and to enhance the sensitivity of the system. In FIG. 1, a spacer 130, mounted on a base plate 132, supports a lens housing 134, which houses an aspheric lens 136 and a plano-convex lens 138, between window 124 and detector housing 128. In addition, the embodiment of FIG. 1 includes a UV filter 140 within detector housing 128, in order to remove any UV excitation radiation that may have exited sample enclosure 106, together with the visible photoluminescent emission of the silica aerogel.

Sensor 100 may include built-in electronics to convert the measured signal intensity directly into the desired units of oxygen concentration, or may be coupled to existing systems that measure other gases. It may also be desirable to incorporate a thermocouple (not shown) into the device 100 of the present invention. This allows easy (and possibly automatic) calibration of the device. As noted, the quenching efficiency of oxygen is a function of temperature. Thus, the signal read by detector 126 can only be converted to oxygen concentration if the temperature is known. It may also be desirable to outfit device 100 with a pressure transducer in order to account for pressure variations at different altitudes, etc.

In operation, lamp 102 is switched on to expose the aerogel 122 to UV radiation. The aerogel 122 then luminesces, emitting visible light of a characteristic spectrum which is transmitted through window 124 to the visible light detector 126. A stream of gas to be measured is passed into the sample enclosure 106 through gas inlet conduit 116 and allowed to contact the aerogel 122. Any oxygen present in the gas sample will quench the photoluminescent emissions from the aerogel by an amount corresponding to the oxygen's partial pressure, thereby reducing the amount of light received by the detector 126.

When used simply to detect a change in oxygen concentration or pressure, the device 100 may require no calibration. Further, thermocouples, pressure transducers and the like may be unnecessary. For such an application, the device 100 may be equipped to notify the user of a change in visible light received at the detector 126 from an initial level, for instance, by an audible or visible alarm.

For applications requiring more precise measurement of oxygen concentration or pressure, some calibration of the device 100 will be necessary. This calibration may be performed by providing two or more gas samples of known oxygen concentration and/or pressure to the photoluminescent silica aerogel 122 in the sample enclosure 106 and recording the responses from detector 126 for each sample. For example, the detector response could be compared for a vacuum and an ambient environment (21% oxygen and approximately 300 millimeters of mercury partial pressure). More precise calibration could be accomplished by measuring the detector responsible for various other relevant oxygen partial pressures. From this data, a graph may be prepared and used to correlate samples of unknown oxygen partial pressure to specific values of known oxygen partial pressure.

While photoluminescent silica aerogels may be used without special treatment in the detectors of this invention, in some cases it may be desirable to specially treat them. For example, when a oxygen detector is to be used in an environment containing liquid water or condensable water vapor, they may be treated with a material that renders the aerogel hydrophobic. This is desirable because silica aerogels are easily degraded upon contact with liquid water. In fact, water can cause the entire silica aerogel structure to collapse on itself and be rendered useless as a detector. In a specific example, the silica aerogels is coated with an organic film following the defect-inducing treatment by exposure to, for instance, hexamethyldisilazane at a temperature of approximately 60° C. for approximately one (1) hour. Such silica aerogel coating techniques are known to those of skill in the art and are described in references such as H. Yokogawa and M. Yokoyama, *J. Non-Cryst. Solids* 1995, v. 186, p. 23–29, incorporated herein by reference for all purposes. Silica aerogels having a hydrophobic coating of this type will function adequately in the devices of the present invention, but may be less sensitive than uncoated silica aerogels. Therefore, they may be preferred only where there is a significant likelihood that the silica aerogel will be contacted by liquid water in a particular application.

An alternative approach is to dry the gaseous samples to be measured by the devices and methods of the present invention. Drying may be accomplished by passing the sample gas over any common desiccant ($CaCl_2$, molecular sieves, $P_2O_5$, CaO) or ZnO prior to introduction into the sample enclosure 106. Thus, in some embodiments, a special chamber will be provided on the feed line to dry samples before they enter the sample enclosure 106.

The devices described herein will generally provide a much faster response time than prior art devices. This is because of the much greater rate of diffusion of gases into the highly porous photoluminescent aerogel matrix relative to non-porous structures such as polymer membranes employed in some conventional oxygen sensors. In addition, the sensors of this invention will often have much longer lifetimes than other oxygen sensors, particularly those susceptible to photo bleaching and to chemical or thermal degradation.

The sensors of the present invention are intended to perform as a low-cost, moderate sensitivity device operating most effectively in the concentration range of 0 to 30 percent oxygen. Of course, they may also be operated at higher concentrations. The sensor operates independently of the nature of the other gases present in the feed gas and of the feed gas flow rate. A preferred embodiment of the sensor of the present invention has been successful operated over a temperature range of –25 to +85 degrees Celsius. The highest sensitivity has been observed at lower temperatures.

The following examples are intended to illustrate various aspects of the present invention, but not to limit its scope.

EXAMPLE 1

Preparation and Properties of Photoluminescent Silica Aerogels

Silica aerogels were prepared by a two-step acid-based catalyzed process using commercially available pre-condensed silica (Silbond H-5, Silbond Corp.). The volume ratios of pre-condensed silica, ethanol (200 proof, from Quantum Corp.), water, and 30 percent ammonia/water ($NH_3/H_2O$) were: 1:1.67:1.5:0.007, respectively. Prior to drying, the wet alcogels (alcohol-containing gels) were aged for 48 hours in a 40 percent $H_2O$/ethanol solution with a pH of approximately 9. Water was removed from the alcogels by several cycles of soaking in pure ethanol. Conversion of the wet alcogels to aerogels followed $CO_2$ substitution and supercritical drying methods, such as those described in P. H. Tewari, A. J. Hunt, K. D. Lofftus, *Mater. Lett.* 3, 363 (1985). The resultant aerogels had a density of approximately 0.08 grams per centimeter cubed ($g/cm^3$).

In preparation for microwave treatments, samples were first dried at approximately 150° C. for approximately 30 minutes, and then placed in a fused-silica tube within the cavity of a commercial microwave oven. The oven nominally delivered 600 watts to the cavity at 2.45 GHz. The tube was then evacuated to about one Pascal (Pa). Residual water, and other volatiles, were removed by applying microwave energy in 5 second pulses until the system maintained a constant pressure. The desired gas was then introduced into the tube at a rate that maintained the system pressure at approximately 500 Pa. Suitable gases included hydrogen and ammonia. Microwave energy was then applied for approximately 60 minutes, although visible photoluminescence was observed in samples after as little as five minutes of treatment.

Figure 2:
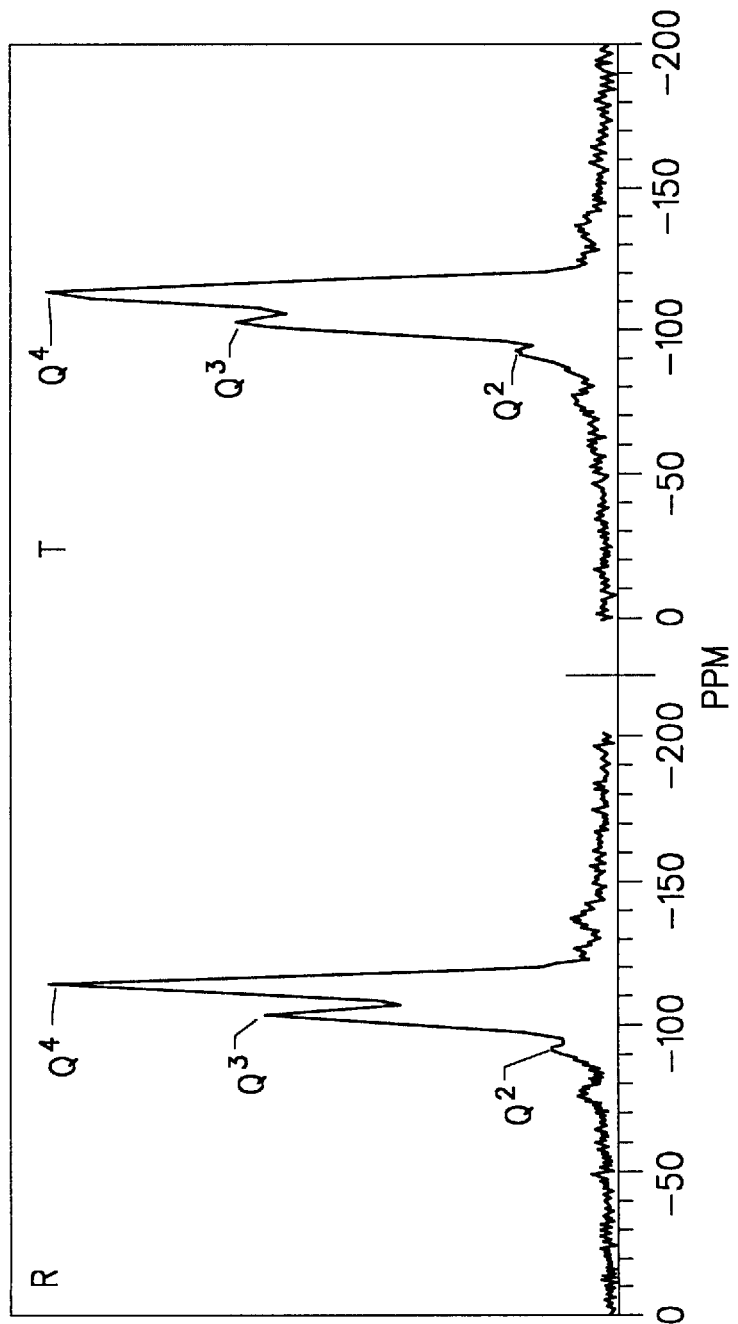
FIG. 2 shows a Si MAS-NMR spectra for native and hydrogen treated silica aerogels.

FIG. 2 shows a Si MAS-NMR spectra for native and hydrogen treated silica aerogels. High surface area silicas contain varying amounts of Si—O—Si bridges. A common notation for these uses "$Q^4$" for ($\equiv$SiO—)$_4$Si, "$Q^3$" for ($\equiv$SiO—)$_3$Si(OH), and "$Q^2$" for ($\equiv$SiO)$_2$Si(OH)$_2$. The untreated silica sample (line R) shows a ratio of $Q^4$:$Q^3$:$Q^2$ typical of a native aerogel. The hydrogen treated sample (line T) contains slightly fewer $Q^4$ groups, relative to the $Q^3$ and $Q^2$ groups. This result indicates that Si—O bond cleavage reactions will preferentially occur at $Q^4$ sites with high bond strain.

Figure 3:
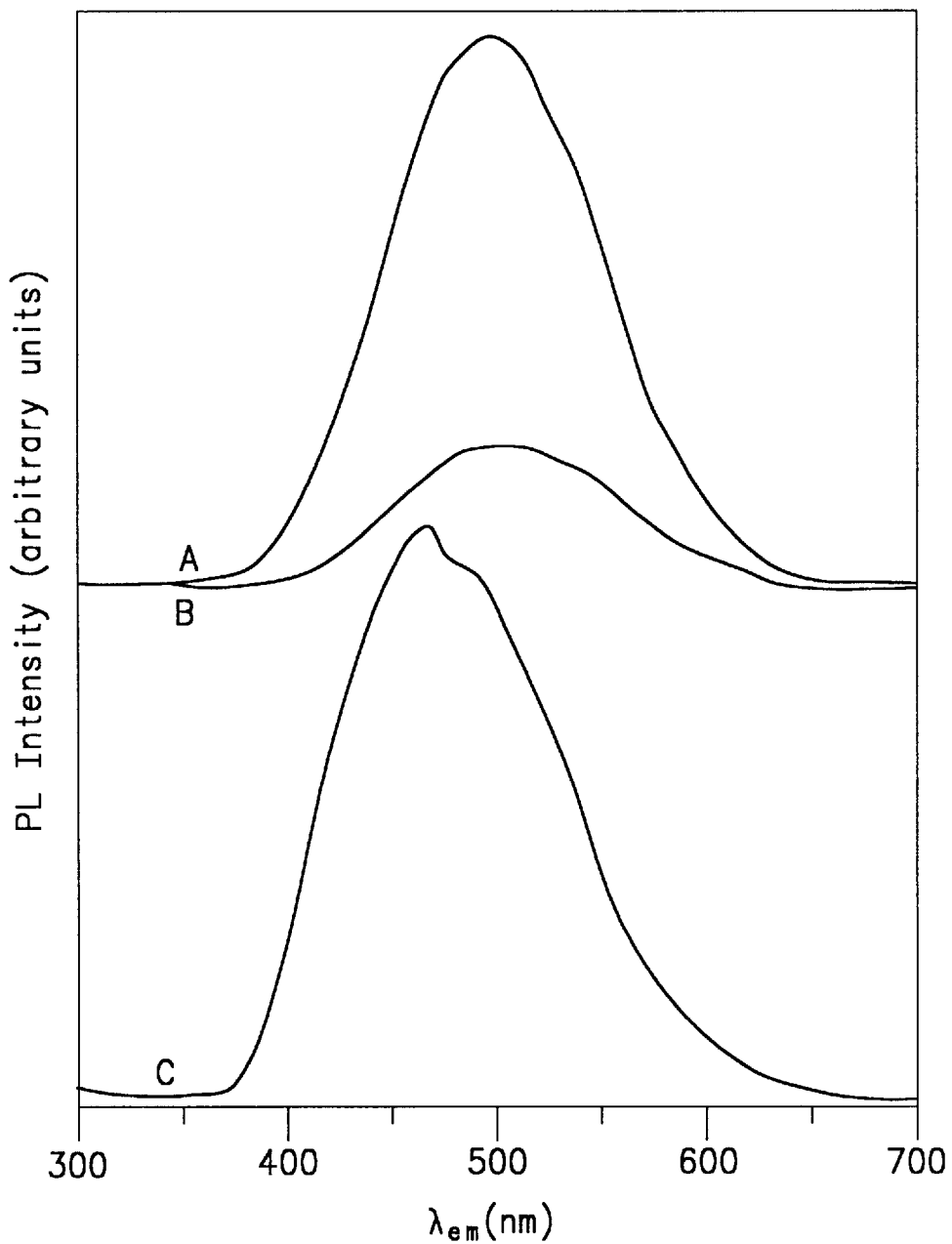
FIGS. 3–6 show results of oxygen determination in accordance with the present invention.

The photoluminescence spectra (PLS) of silica aerogels treated with energized hydrogen and ammonia ($NH_3$) appear in FIG. 3. The photoluminescence requires an excitation wavelength of 300–400 nm. The emission band maxima for the $H_2$ and $NH_3$ treated samples lie at 490 and 460 nanometers, respectively. A hydrogen treated sample is represented by line A on the graph and an ammonia treated sample is represented by line C in the figure. Thermal treatment of the photoluminescent aerogels under Ar up to 800° C. was found to not alter the emission wavelength. However, heating the aerogels under air to 600° C. resulted in the loss of the photoluminescence. This is consistent with the theory that photoluminescence results from the localized oxygen deficiencies (defects) within the material.

That the presence of molecular oxygen within an aerogel strongly quenches its photoluminescence, is also illustrated in FIG. 3. The intensity of photoluminescence of the treated aerogel in the absence of oxygen (line A) was found to be 12.5 times greater than that of the same sample in pure oxygen at 101 kPa (line B).

EXAMPLE 2

Variability of Photoluminescent Intensity with Temperature and Pressure

Figure 4:
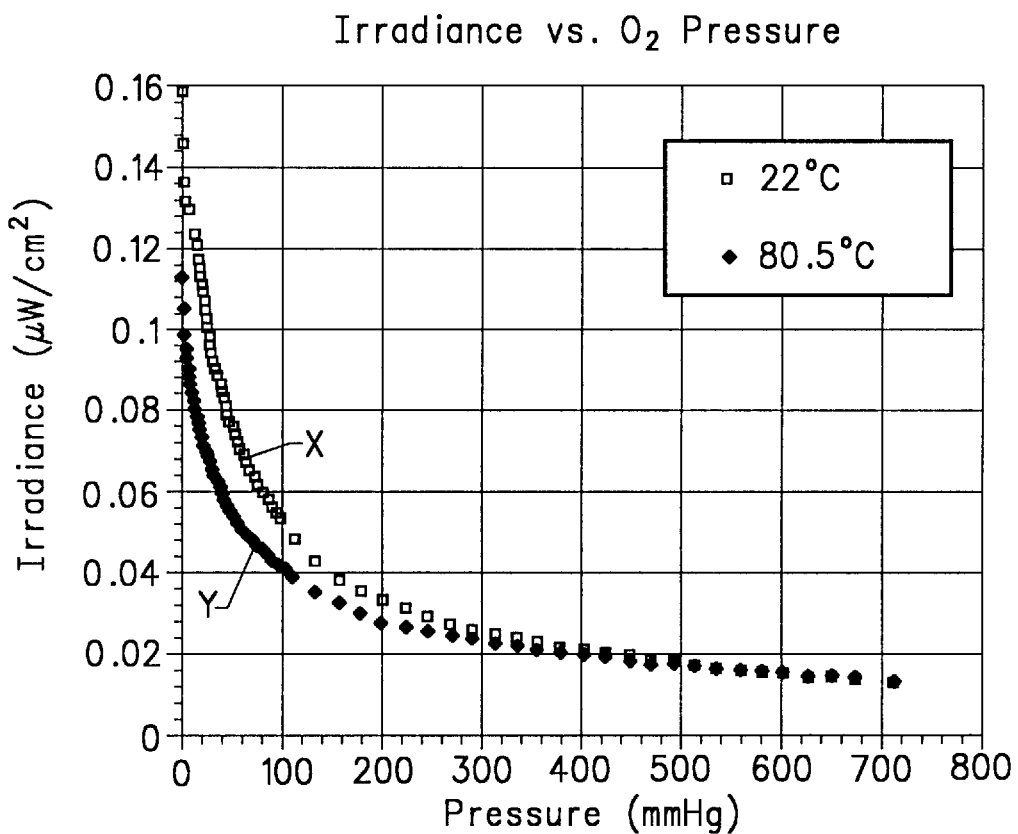

FIG. 4 shows a graph of measured photoluminescence intensity (irradiance) versus total oxygen pressure for an oxygen concentration of 100% at two temperatures, using a detector of the same construction as illustrated in FIG. 1. The graph demonstrates that photoluminescence intensity varies inversely with ambient temperature since line X represents irradiance at 22° C. while line Y represents irradiance at 80.5° C. A plot of irradiance versus oxygen concentration (not shown) provides similar results.

EXAMPLE 3

Hydrophobic Treatment of Photoluminescent Silica Aerogels

Figure 5:
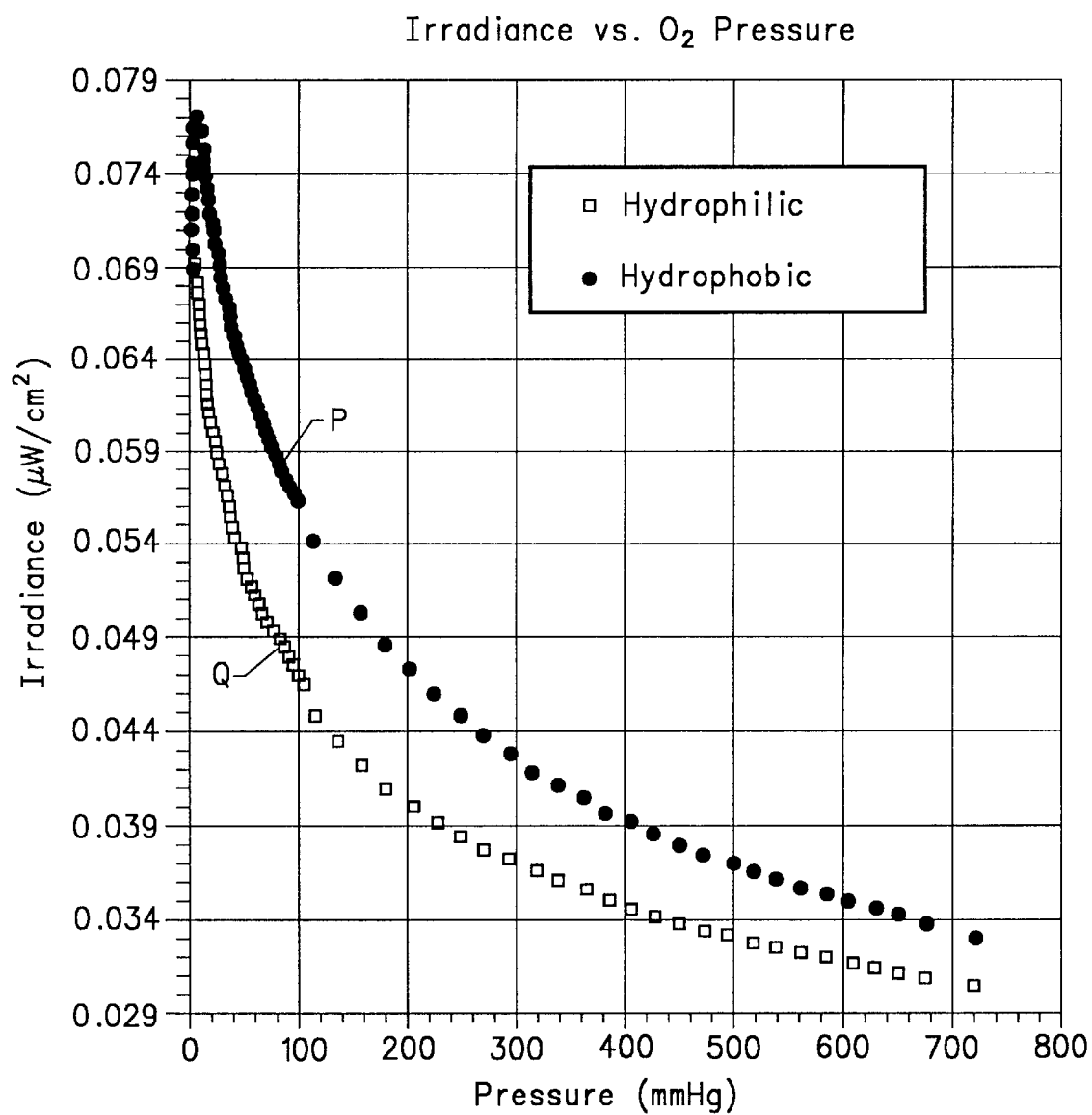

FIG. 5 shows a plot of photoluminescence intensity (irradiance) versus oxygen ($O_2$) partial pressure for two aerogels. Line P represents a hydrophilic (untreated) photoluminescent silica aerogel. Line Q represents a photoluminescent aerogel coated with a hydrophobic organic coating. The graph of the figure demonstrates the slightly reduced sensitivity of the treated aerogel relative to the untreated material; that is, the coated aerogel has a narrower range of response. Note however that the water repellent aerogel still exhibits good sensitively, certainly suitable for most applications.

EXAMPLE 4

Pressure Gage Application

Figure 6:
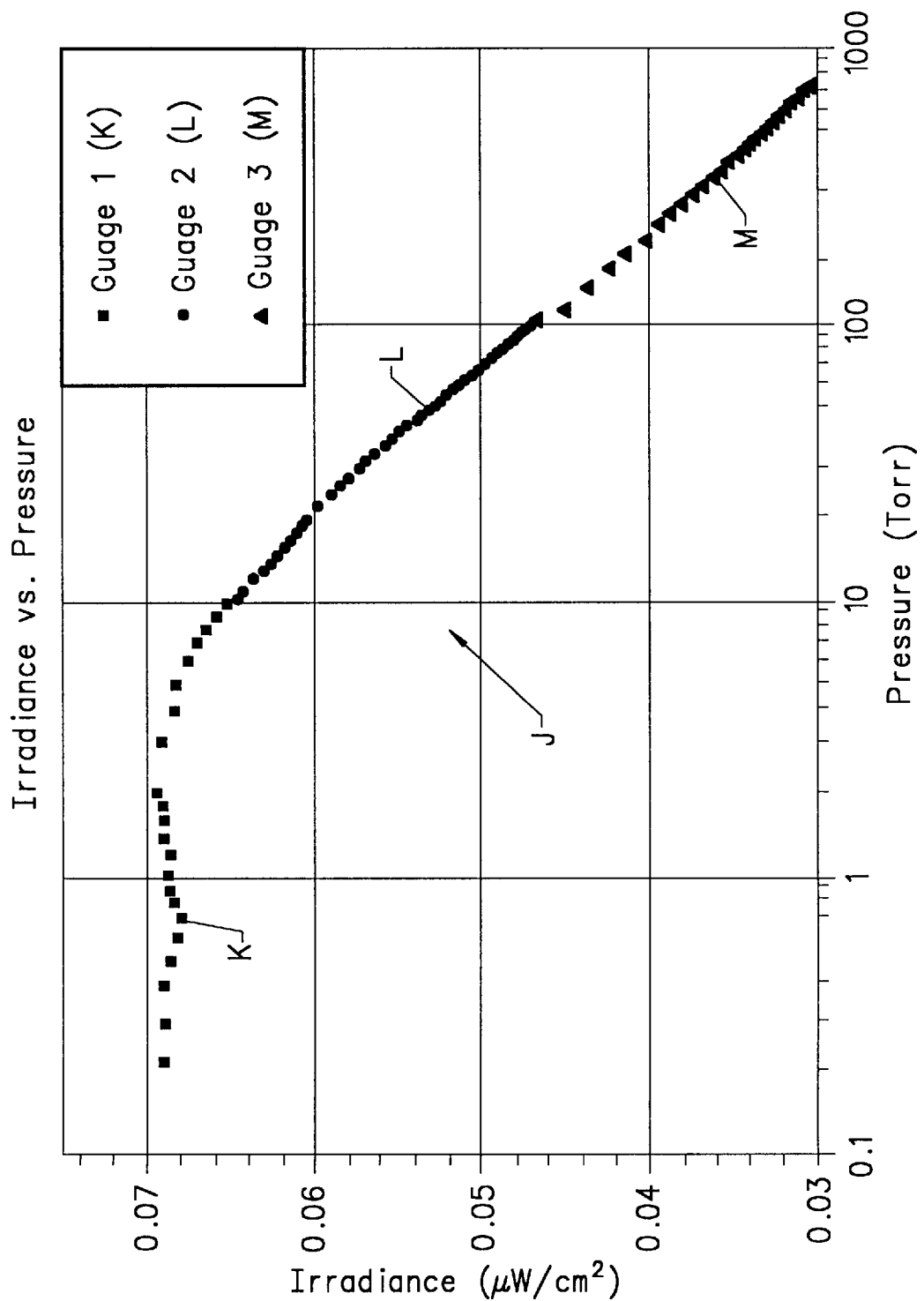

FIG. 6 demonstrates one potential application of the present invention. FIG. 6 is a graph of irradiance versus total pressure of an oxygen containing gas. Line J shows the decrease in irradiance with increasing pressure of the gas sample. Superimposed upon line J are segments K, L, and M which represent pressure measurements taken using conventional pressure gages. The multiple segments K, L, and M are necessary because conventional pressure gages operate over limited ranges of pressures. Since the present invention operates accurately over a very large range of pressures, it may serve as a pressure gauge operable over a much greater total pressure range than conventional gauges. In effect, a single photoluminescent aerogel oxygen sensor may replace three or more conventional devices which would otherwise be required.

Oxygen sensors according to the present invention may find use in a variety of fields. For example, they may be used in pressure gauges; in medical applications, such as in the measurement of respiratory gases; in industrial and chemical process, such as the fermentation industry; in combustion applications, for instance, in automobile engines, furnaces, kilns, etc.; in the space program, for instance, for detecting the inadvertent mixing of rocket fuels; and generally anywhere where the presence of oxygen or its quantification are of concern.

The present invention has been described in terms of a preferred embodiment and sample applications. The invention however is not limited by the embodiments and applications described.

Although a specific embodiment of the present invention has been described in detail, it should be understood that the present invention may be embodied in many other specific forms without departing from the spirit or scope of the invention as recited in the claims.

What is claimed is:

1. An oxygen sensing device, comprising:
   a support;
   a photoluminescent aerogel material disposed on said support;
   a source of radiation capable of providing excitation energy to said aerogel;
   a detector capable of detecting light emitted from the aerogel; and
   an interface capable of bringing a gas phase sample into contact with said aerogel;
   whereby, oxygen contained in said sample reduces photoluminescent emissions from said aerogel by an amount related to the oxygen concentration or pressure in said sample.

2. The device of claim 1, wherein said photoluminescent aerogel material is a monolith.

3. The device of claim 1, wherein said photoluminescent aerogel material is a powder.

4. The device of claim 3, wherein said powder is distributed in a mesh substrate.

5. The device of claim 3, wherein said powder is distributed on a continuous substrate.

6. The device of claim 1, wherein said photoluminescent silica aerogel material is a monolith bound to a substrate.

7. The device of claim 1, wherein said source of radiation emits radiation in the ultraviolet region of the electromagnetic spectrum.

8. The device of claim 7, wherein said ultraviolet radiation emitter is a mercury-arc lamp.

9. The device of claim 7, wherein said ultraviolet radiation emitter is an ultraviolet radiation emitting diode.

10. The device of claim 1, wherein said detector is capable of detecting visible light.

11. The device of claim 10 wherein said detector is a silicon photodiode.

12. The device of claim 1, further comprising a converter for generating a value of oxygen concentration and/or pressure from the light level detected by said detector.

13. The device of claim 1 further comprising a signal generator, which signal generator signals a change in oxygen concentration or pressure in a gas phase sample detected by said detector.

14. The device of claim 13, wherein said signal generator generates an audible or visible signal.

15. The device of claim 1, wherein the photoluminescent aerogel material is a silica aerogel.

16. An oxygen sensing device, comprising:
    a light proof housing;
    a photoluminescent silica aerogel material disposed within a sample enclosure within said housing;
    a first window in said sample enclosure, said window providing an entry for ultraviolet radiation into said sample enclosure;
    a second window in said sample enclosure providing an exit for visible light emitted from said aerogel within said sample enclosure;
    a source of ultraviolet radiation disposed adjacent to said first window in said sample enclosure;
    a detector capable of detecting visible light emitted from said aerogel through said second window in said sample enclosure;
    a conduit having access to said sample enclosure and capable of bringing a gas phase sample into contact with said aerogel within said sample enclosure,
    whereby oxygen in said sample reduces photoluminescent emissions from said aerogel by an amount related to the oxygen concentration or pressure in said sample.

17. The device of claim 16, further comprising at least one optical element disposed between said second window and said detector, whereby said at least one optical element optically modifies photoluminescent emissions of said photoluminescent silica aerogel material.

18. The device of claim 17 wherein said at least one optical element comprises a spherical lens or plano convex lens.

19. The device of claim 17 wherein said at least one optical element comprises a UV radiation filter.

20. The device of claim 16, further comprising a thermocouple.

21. The device of claim 16 wherein said photoluminescent silica aerogel is oriented so as to maximally expose a principle surface to both the UV radiation source and the visible light detector.

22. The device of claim 16 wherein said sample conduit further comprises a desiccation zone for drying a gas sample prior to bringing it into contact with the photoluminescent silica aerogel.

23. The device of claim 16, further comprising a converter for generating a value of oxygen concentration and/or pressure from the light level detected by said detector.

24. The device of claim 16 further comprising a signal generator, which signal generator responds to a change in oxygen concentration or pressure in a gas phase sample detected by said detector.

25. A method for determining a change in concentration and/or pressure of oxygen in a gas phase sample, comprising:

provicing a photoluminescent aerogel material;

irradiating said photoluminescent aerogel material with a source of excitation energy;

bringing an oxygen-containing gas phase sample into contact with said photoluminescent aerogel; and detecting light emitted from said photoluminescent aerogel in the presence of said gas phase sample.

26. The method of claim 25, further comprising converting the light detected by said detector to oxygen pressure and/or concentration values.

27. The method of claim 26, further comprising calibrating said device with samples of known oxygen concentration and/or pressure prior to bringing said oxygen-containing gas phase sample into contact with said photoluminescent aerogel.

28. The method of claim 25 further comprising signaling a change in oxygen concentration or pressure in a gas phase sample.

29. The method of claim 25 further comprising:

separately bringing at least two gas phase samples of known and different oxygen concentrations and/or pressures into contact with said photoluminescent aerogel;

detecting visible light emitted from said photoluminescent aerogel in the presence of each of said gas phase samples of known and different oxygen concentrations and/or pressures; and determining a calibration relationship between the visible light emitted from said photoluminescent aerogel and the known oxygen concentration and pressures of said at least two gas phase samples.

30. The device of claim 1, wherein the phooluminescent aerogel material comprises:

a photoluminescene silica acrogel; and a hydrophobic coating on said aerogel.

31. The device of clairnl 30 wherein said hydrophobic coating is an organic material.

32. The device of claim 31 wherein said organic material is a deposition product of hexamethyldisilazane.

* * * * *